US009606254B2

United States Patent
Cheng et al.

(10) Patent No.: US 9,606,254 B2
(45) Date of Patent: Mar. 28, 2017

(54) DETERMINING CEMENT IMPEDANCE FROM A FORMATION BOUNDARY

(71) Applicant: HALLIBURTON ENERGY SERVICES, INC., Houston, TX (US)

(72) Inventors: Arthur Chuen Hon Cheng, Houston, TX (US); Mark Elliott Willis, Katy, TX (US); Tatiana Gilstrap, The Woodlands, TX (US); Robert Eric Epstein, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/418,737

(22) PCT Filed: Jul. 15, 2014

(86) PCT No.: PCT/US2014/046752
§ 371 (c)(1),
(2) Date: Jan. 30, 2015

(87) PCT Pub. No.: WO2015/023385
PCT Pub. Date: Feb. 19, 2015

(65) Prior Publication Data
US 2016/0033664 A1    Feb. 4, 2016

Related U.S. Application Data

(60) Provisional application No. 61/866,092, filed on Aug. 15, 2013.

(51) Int. Cl.
*E21B 33/00*    (2006.01)
*G01V 1/48*    (2006.01)
(Continued)

(52) U.S. Cl.
CPC ............... *G01V 1/48* (2013.01); *E21B 47/00* (2013.01); *E21B 47/0005* (2013.01);
(Continued)

(58) Field of Classification Search
CPC ...... E21B 47/0002; E21B 44/00; E21B 47/00; E21B 47/01; G01N 2291/044
(Continued)

(56) References Cited

U.S. PATENT DOCUMENTS 3,175,639 A    3/1965   Liben
3,399,745 A *   9/1968   Sparks .................... G01V 1/00
                                                                          181/122
(Continued)

FOREIGN PATENT DOCUMENTS

WO           99/31354          6/1999
WO    WO 2013/081608    6/2013

OTHER PUBLICATIONS

International Search Report and Written Opinion of the International Searching Authority issued in International Application No. PCT/US2014/046752 on Nov. 21, 2014; 10 pages.
(Continued)

*Primary Examiner* — Eric S McCall
*Assistant Examiner* — Mohammed E Keramet-Amircolai
(74) *Attorney, Agent, or Firm* — Benjamin Fite; Parker Justiss, P.C.

(57) ABSTRACT

Systems, methods, and software for determining properties of a medium surrounding an exterior portion of a well casing are described. In some aspects, the properties of the medium are determined based on measurements of detected acoustic energy and distances between one or more acoustic transmitters and two or more acoustic receivers. The measurements are obtained based on operating the transmitters and the receivers within a wellbore that includes the well casing.

19 Claims, 10 Drawing Sheets

(51) Int. Cl.
*E21B 47/00* (2012.01)
*G01V 1/30* (2006.01)
*G01V 1/44* (2006.01)
*E21B 47/10* (2012.01)
*G01N 33/38* (2006.01)
*G01V 1/52* (2006.01)

(52) U.S. Cl.
CPC ......... *E21B 47/101* (2013.01); *G01N 33/383* (2013.01); *G01V 1/306* (2013.01); *G01V 1/44* (2013.01); *G01V 1/52* (2013.01)

(58) Field of Classification Search
USPC .......................... 73/152.57, 152.43, 152.44
See application file for complete search history.

(56) References Cited

U.S. PATENT DOCUMENTS

| | | | |
|---|---|---|---|
| 3,883,841 A | 5/1975 | Norel et al. | |
| 4,869,338 A | 9/1989 | Wiggins et al. | |
| 5,278,805 A | 1/1994 | Kimball | |
| 5,763,773 A | 6/1998 | Birchak et al. | |
| 6,850,462 B2 | 2/2005 | McDaniel et al. | |
| 7,525,872 B2* | 4/2009 | Tang | G01V 1/50 181/105 |
| 7,773,454 B2* | 8/2010 | Barolak | E21B 47/0005 181/105 |
| 7,957,905 B2* | 6/2011 | Heigl | G01V 1/48 702/11 |
| 8,157,008 B2* | 4/2012 | Lilley | E21B 37/00 166/177.4 |
| 2003/0139884 A1 | 7/2003 | Blanch et al. | |
| 2006/0285439 A1* | 12/2006 | Haugland | G01V 1/48 367/75 |
| 2007/0211572 A1 | 9/2007 | Reiderman et al. | |
| 2010/0126718 A1* | 5/2010 | Lilley | E21B 37/00 166/177.4 |
| 2011/0134719 A1* | 6/2011 | Kinoshita | G01V 1/48 367/31 |
| 2011/0180327 A1 | 7/2011 | Bittar et al. | |
| 2011/0231097 A1* | 9/2011 | Market | G01V 1/48 702/6 |
| 2012/0069713 A1* | 3/2012 | Geerits | G01V 1/48 367/99 |
| 2013/0075091 A1* | 3/2013 | Hallundbæk | E21B 47/01 166/250.15 |
| 2013/0155812 A1 | 6/2013 | Froelich et al. | |

OTHER PUBLICATIONS

Aki et al., "Quantitative Seismology", University Science Books, 2nd edition, published in 2002, 2 pages.
Claerbout et al., "Basic Earth Imaging", Oct. 31, 2005, 236 pages.
Patent Examination Report No. 1 issued in Australian Application No. 2014307022, dated May 4, 2016.
Patent Examination Report No. 2 issued in Australian Application No. 2014307022, dated Jun. 2, 2016.

\* cited by examiner

DETERMINING CEMENT IMPEDANCE FROM A FORMATION BOUNDARY

CLAIM OF PRIORITY

This application is a U.S. National Stage of International Application No. PCT/US2014/046752, filed Jul. 15, 2014, which claims priority to U.S. Patent Application No. 61/866,092 filed on Aug. 15, 2013, the entire contents of which are hereby incorporated by reference.

BACKGROUND

This disclosure relates to ultrasonic cement evaluation tools.

Cement evaluation tools can be used to assess the properties of pipe casing, cement, and other well structures during oil field drilling and/or formation evaluation operations. Conventional casing/cement evaluation tools and methodologies typically use a single source/receiver geometry in a pulse-echo mode to obtain the casing thickness and the impedance of the cement. Other methodologies use the decay (or attenuation) of the sonic waveform across two receivers to provide an empirical measurement of the cement bonding between the casing and the cement.

DESCRIPTION OF DRAWINGS

Like reference symbols in the various drawings indicate like elements.

DETAILED DESCRIPTION

Figure 1A:
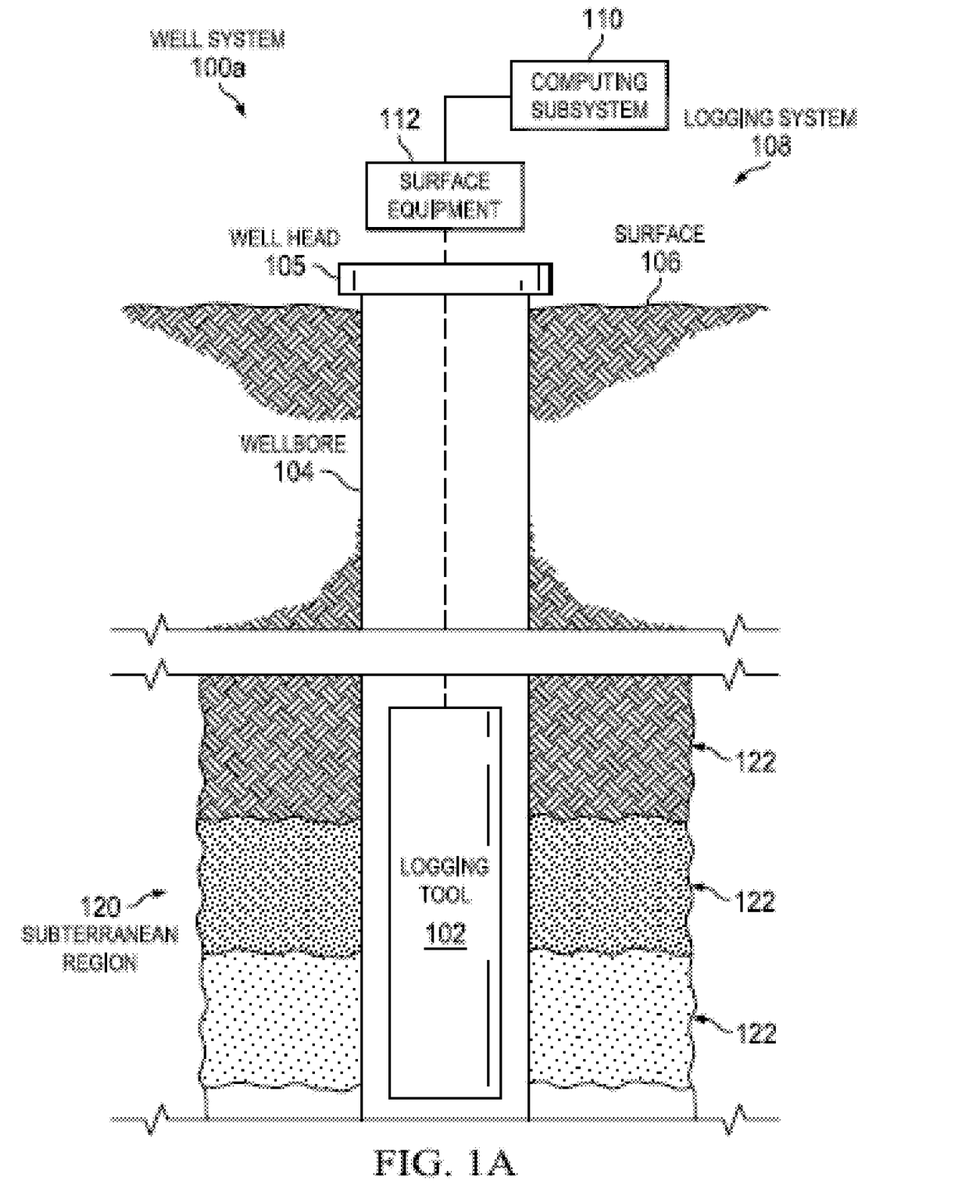
FIG. 1A is a diagram of an example well system.

FIG. 1A is a diagram of an example well system 100a. The example well system 100a includes a logging system 108 and a subterranean region 120 beneath the ground surface 106. A well system can include additional or different features that are not shown in FIG. 1A. For example, the well system 100a may include additional drilling system components, wireline logging system components, etc.

The subterranean region 120 can include all or part of one or more subterranean formations or zones. The example subterranean region 120 shown in FIG. 1A includes multiple subsurface layers 122 and a wellbore 104 penetrated through the subsurface layers 122. The subsurface layers 122 can include sedimentary layers, rock layers, sand layers, or combinations of these other types of subsurface layers. One or more of the subsurface layers can contain fluids, such as brine, oil, gas, etc. Although the example wellbore 104 shown in FIG. 1A is a vertical wellbore, the logging system 108 can be implemented in other wellbore orientations. For example, the logging system 108 may be adapted for horizontal wellbores, slant wellbores, curved wellbores, vertical wellbores, or combinations of these.

The example logging system 108 includes a logging tool 102, surface equipment 112, and a computing subsystem 110. In the example shown in FIG. 1A, the logging tool 102 is a downhole logging tool that operates while disposed in the wellbore 104. The example surface equipment 112 shown in FIG. 1A operates at or above the surface 106, for example, near the well head 105, to control the logging tool 102 and possibly other downhole equipment or other components of the well system 100. The example computing subsystem 110 can receive and analyze logging data from the logging tool 102. A logging system can include additional or different features, and the features of a logging system can be arranged and operated as represented in FIG. 1A or in another manner.

In some instances, all or part of the computing subsystem 110 can be implemented as a component of, or can be integrated with one or more components of, the surface equipment 112, the logging tool 102, or both. In some cases, the computing subsystem 110 can be implemented as one or more discrete computing system structures separate from the surface equipment 112 and the logging tool 102.

In some implementations, the computing subsystem 110 is embedded in the logging tool 102, and the computing subsystem 110 and the logging tool 102 can operate concurrently while disposed in the wellbore 104. For example, although the computing subsystem 110 is shown above the surface 106 in the example shown in FIG. 1A, all or part of the computing subsystem 110 may reside below the surface 106, for example, at or near the location of the logging tool 102.

The well system 100a can include communication or telemetry equipment that allow communication among the computing subsystem 110, the logging tool 102, and other components of the logging system 108. For example, the components of the logging system 108 can each include one or more transceivers or similar apparatus for wired or wireless data communication among the various components. For example, the logging system 108 can include systems and apparatus for wireline telemetry, wired pipe telemetry, mud pulse telemetry, acoustic telemetry, electromagnetic telemetry, or a combination of these other types of telemetry. In some cases, the logging tool 102 receives commands, status signals, or other types of information from the computing subsystem 110 or another source. In some cases, the computing subsystem 110 receives logging data, status signals, or other types of information from the logging tool 102 or another source.

Logging operations can be performed in connection with various types of downhole operations at various stages in the lifetime of a well system. Structural attributes and components of the surface equipment 112 and logging tool 102 can be adapted for various types of logging operations. For example, logging may be performed during drilling operations, during wireline logging operations, or in other contexts. As such, the surface equipment 112 and the logging tool 102 may include, or may operate in connection with drilling equipment, wireline logging equipment, or other equipment for other types of operations.

Figure 1B:
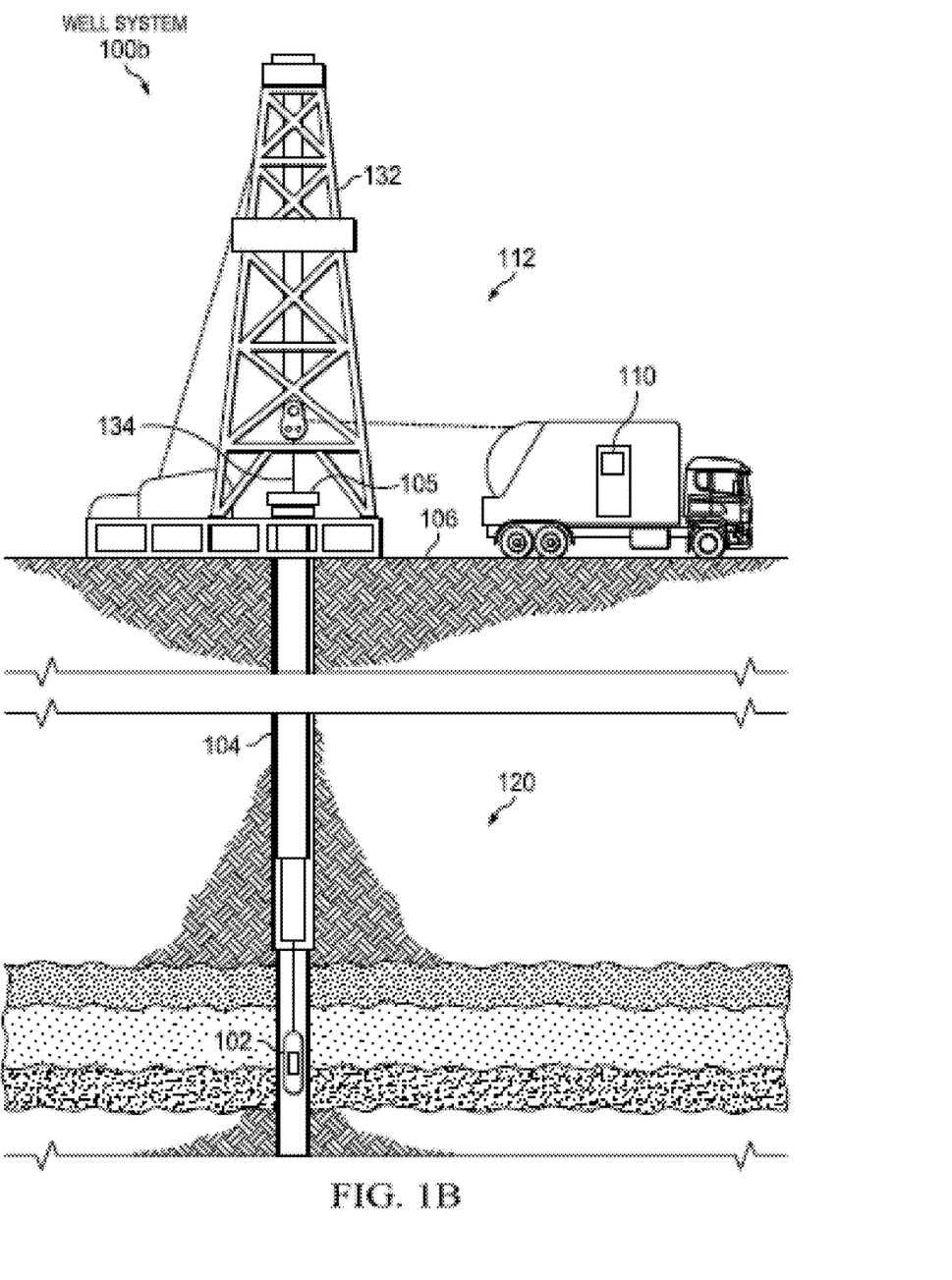
FIG. 1B is a diagram of an example well system that includes a logging tool in a wireline logging environment.

In some examples, logging operations are performed during wireline logging operations. FIG. 1B shows an example well system 100b that includes the logging tool 102 in a wireline logging environment. In some example wireline logging operations, the surface equipment 112 includes a platform above the surface 106 that is equipped with a derrick 132 that supports a wireline cable 134 that extends into the wellbore 104. Wireline logging operations can be performed, for example, after a drilling string is removed from the wellbore 104, to allow the wireline logging tool 102 to be lowered by wireline or logging cable into the wellbore 104.

Figure 1C:
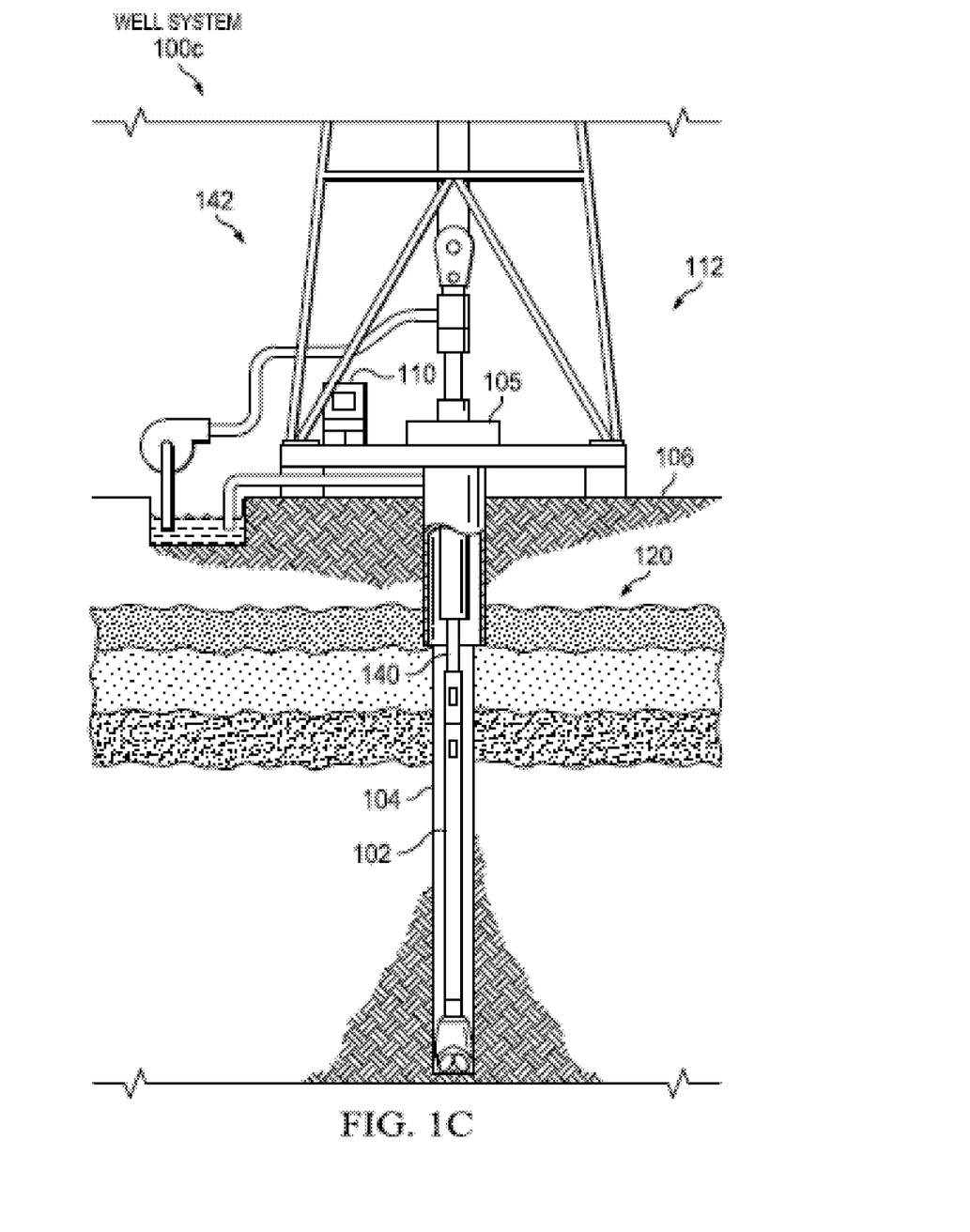
FIG. 1C is a diagram of an example well system that includes a logging tool in a logging while drilling (LWD) environment.

In some examples, logging operations are performed during drilling operations. FIG. 1C shows an example well system 100*c* that includes the logging tool 102 in a logging while drilling (LWD) environment. Drilling is commonly carried out using a string of drill pipes connected together to form a drill string 140 that is lowered through a rotary table into the wellbore 104. In some cases, a drilling rig 142 at the surface 106 supports the drill string 140, as the drill string 140 is operated to drill a wellbore penetrating the subterranean region 120. The drill string 140 may include, for example, a kelly, drill pipe, a bottom hole assembly, and other components. The bottom hole assembly on the drill string may include drill collars, drill bits, the logging tool 102, and other components. The logging tools may include measuring while drilling (MWD) tools, LWD tools, and others.

As shown, for example, in FIG. 1B, the logging tool 102 can be suspended in the wellbore 104 by a coiled tubing, wireline cable, or another structure that connects the tool to a surface control unit or other components of the surface equipment 112. In some example implementations, the logging tool 102 is lowered to the bottom of a region of interest and subsequently pulled upward (e.g., at a substantially constant speed) through the region of interest. As shown, for example, in FIG. 1C, the logging tool 102 can be deployed in the wellbore 104 on jointed drill pipe, hard wired drill pipe, or other deployment hardware. In some example implementations, the logging tool 102 collects data during drilling operations as it moves downward through the region of interest during drilling operations. In some example implementations, the logging tool 102 collects data while the drilling string 140 is moving, for example, while it is being tripped in or tripped out of the wellbore 104.

In some example implementations, the logging tool 102 collects data at discrete logging points in the wellbore 104. For example, the logging tool 102 can move upward or downward incrementally to each logging point at a series of depths in the wellbore 104. At each logging point, instruments in the logging tool 102 perform measurements on the subterranean region 120. The measurement data can be communicated to the computing subsystem 110 for storage, processing, and analysis. Such data may be gathered and analyzed during drilling operations (e.g., during logging while drilling (LWD) operations), during wireline logging operations, or during other types of activities.

The computing subsystem 110 can receive and analyze the measurement data from the logging tool 102 to detect properties of various subsurface layers 122. For example, the computing subsystem 110 can identify the density, material content, or other properties of the subsurface layers 122 based on the measurements acquired by the logging tool 102 in the wellbore 104.

Figure 2:
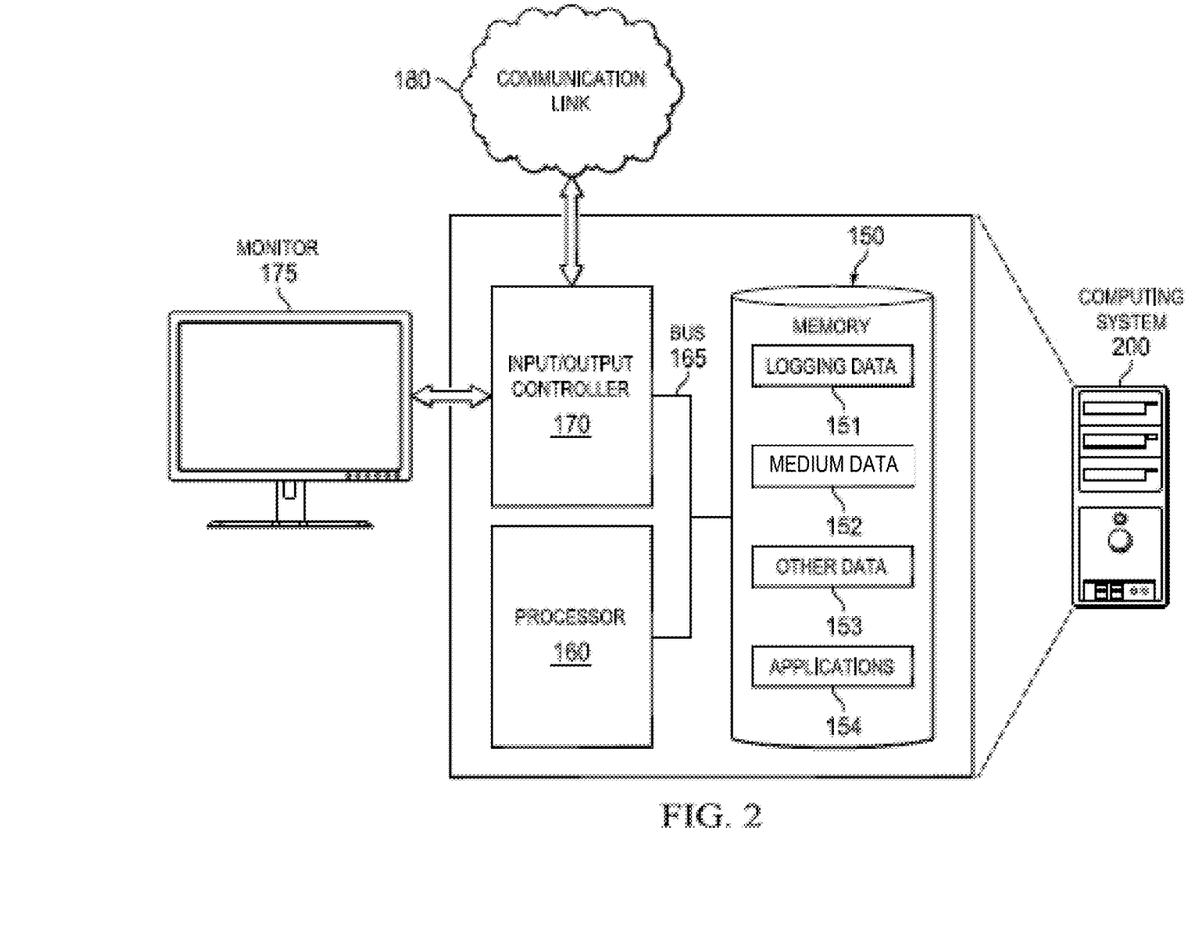
FIG. 2 is a diagram of an example computing system.

FIG. 2 is a diagram of the example computing system 200. The example computing system 200 can be used as the computing subsystem 110 of FIG. 1A, 1B, or 1C, or the example computing system 200 can be used in another manner. In some cases, the example computing system 200 can operate in connection with a well system (e.g., the well systems 100*a*, 100*b*, or 100*c* shown in FIG. 1A, 1B, or 1C) and be located at or near one or more wells of a well system or at a remote location. All or part of the computing system 200 may operate independent of a well system.

The example computing system 200 shown in FIG. 2 includes a memory 150, a processor 160, and input/output controllers 170 communicably coupled by a bus 165. The memory 150 can include, for example, a random access memory (RAM), a storage device (e.g., a writable read-only memory (ROM) or others), a hard disk, or another type of storage medium. The computing subsystem 110 can be preprogrammed or it can be programmed (and reprogrammed) by loading a program from another source (e.g., from a CD-ROM, from another computer device through a data network, or in another manner).

In some examples, the input/output controller 170 is coupled to input/output devices (e.g., a monitor 175, a mouse, a keyboard, or other input/output devices) and to a communication link 180. The input/output devices receive and transmit data in analog or digital form over communication links such as a serial link, a wireless link (e.g., infrared, radio frequency, or others), a parallel link, or another type of link.

The communication link 180 can include any type of communication channel, connector, data communication network, or other link. For example, the communication link 180 can include a wireless or a wired network, a Local Area Network (LAN), a Wide Area Network (WAN), a private network, a public network (such as the Internet), a WiFi network, a network that includes a satellite link, or another type of data communication network.

The memory 150 can store instructions (e.g., computer code) associated with an operating system, computer applications, and other resources. The memory 150 can also store application data and data objects that can be interpreted by one or more applications or virtual machines running on the computing system 200. As shown in FIG. 2, the example memory 150 includes logging data 151, medium data 152, other data 153, and applications 154. The data and applications in the memory 150 can be stored in any suitable form or format.

The logging data 151 can include measurements and other data from a logging tool. In some cases, the logging data 151 include one or more measurements for each of multiple different logging points in a wellbore. For example, the logging point associated with a given measurement can be the location of the logging tool's reference point when the given measurement was acquired. Each measurement can include data obtained by one or more transmitter-receiver pairs operating at one or more signal frequencies. Each measurement can include data obtained by multiple transmitter-receiver pairs operating at one or more transmitter-receiver spacings. The logging data 151 can include information identifying a transmitter-receiver spacing associate with each measurement.

The medium data 152 can include information on a medium, e.g., cement or formation. For example, the medium data 152 can include information describing the impedance, resistivity, size, depth, volume, geometry, areal extent, porosity, pressure, density, shear modulus, and other information on a medium. In some implementations, the medium data 152 includes information generated by an inversion engine. For example, the medium data 152 may include density of the medium derived from measurements and other information in the logging data 151. Accordingly, the medium data 152 may include information associated with one or more logging points.

The other data 153 can include other information that is used by, generated by, or otherwise associated with the applications 154. For example, the other data 153 can include simulated data or other information that can be used by an inversion engine to produce the medium data 152 from the logging data 151.

The applications 154 can include software applications, scripts, programs, functions, executables, or other modules that are interpreted or executed by the processor 160. For example, the applications 154 can include an inversion engine and other types of modules. The applications 154 may include machine-readable instructions for performing one or more of the operations related to FIG. 8, which is discussed in detail below.

The applications 154 can obtain input data, such as logging data, simulation data, or other types of input data, from the memory 150, from another local source, or from one or more remote sources (e.g., via the communication link 180). The applications 154 can generate output data and store the output data in the memory 150, in another local medium, or in one or more remote devices (e.g., by sending the output data via the communication link 180).

The processor 160 can execute instructions, for example, to generate output data based on data inputs. For example, the processor 160 can run the applications 154 by executing or interpreting the software, scripts, programs, functions, executables, or other modules contained in the applications 154. The processor 160 may perform one or more of the operations related to FIG. 8. The input data received by the processor 160 or the output data generated by the processor 160 can include any of the logging data 151, the medium data 152, or the other data 153.

In some implementations, the logging tool 102 of FIGS. 1A, 1B, and 1C includes an ultrasonic cement evaluation tool. Example ultrasonic cement evaluation tools are shown in FIGS. 3, 4, 5, and 6. An ultrasonic cement evaluation tool may be used to measure properties of the cement, casing, other well structures, and underlying earth formations. The cement evaluation tool may include one or more ultrasonic arrays to generate energy at the surrounding structures and to detect acoustic energy returning from the surrounding structures. The cement evaluation tool may include an electronic processor to determine information about the structures based on the detected returning acoustic energy. The arrays may be directly coupled to the casing using a pad device, or may be mounted on or within a logging tool. Each ultrasonic array may include one or more ultrasonic or high frequency (e.g., greater than 500 kHz) acoustic sources (e.g., acoustic transmitters).

In some implementations, the cement evaluation tool generates ultrasonic acoustic energy, and conducts measurements based on a ray approximation analysis of the acoustic propagation. During usage, the ultrasonic acoustic energy is propagated into the casing, and the reflections from the casing/cement/formation interfaces are measured using an array of receivers. The measurements may be used to quantify cement properties, such as the shear modulus and density of the cement. The cement evaluation tool may provide sufficient resolution and information about the cement/formation or cement/second casing interfaces of a well structure to properly quantify the cement properties. An array of sources and receivers may be used to obtain a clear definition of the casing/cement and cement/formation/second casing interfaces, as well as to obtain both the compressional and shear moduli of the cement. Measurements and/or processed data from the tool may be transmitted through a support cable to a surface control system, where they are reviewed by an operator. In some implementations, either additionally or alternatively, measurements may be stored within the tool (e.g., in a data storage device) for future retrieval, processing, and/or review at the surface. In one or more implementations, the measurements and/or processed data from the tool may be transmitted via other communication schemes (e.g. mud-pulse telemetry, wired pipe, electromagnetic telemetry, acoustic telemetry, and/or other telemetry schemes) used downhole.

Figure 3:
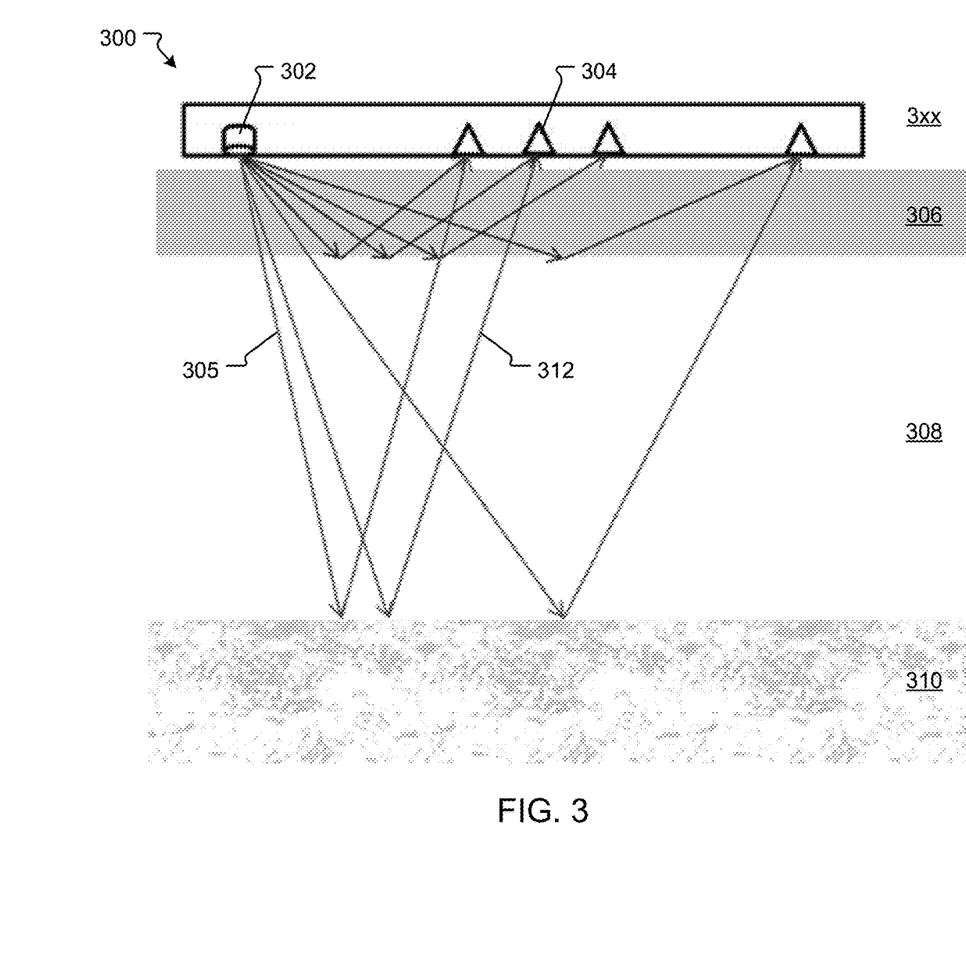
FIGS. 3 and 4 show example implementations of a cement evaluation tool.

Referring to FIG. 3, an example configuration of a cement evaluation tool 300 includes an array with a single transmitter 302 positioned to the side of multiple receivers 304. Acoustic energy 305 generated by the transmitter 302 reflects from the interfaces between the casing 306 and cement 308 or between the cement 308 and the formation 310, and returns to the tool 300. Returning energy 312 is detected by one or more of the receivers 304.

Figure 4:
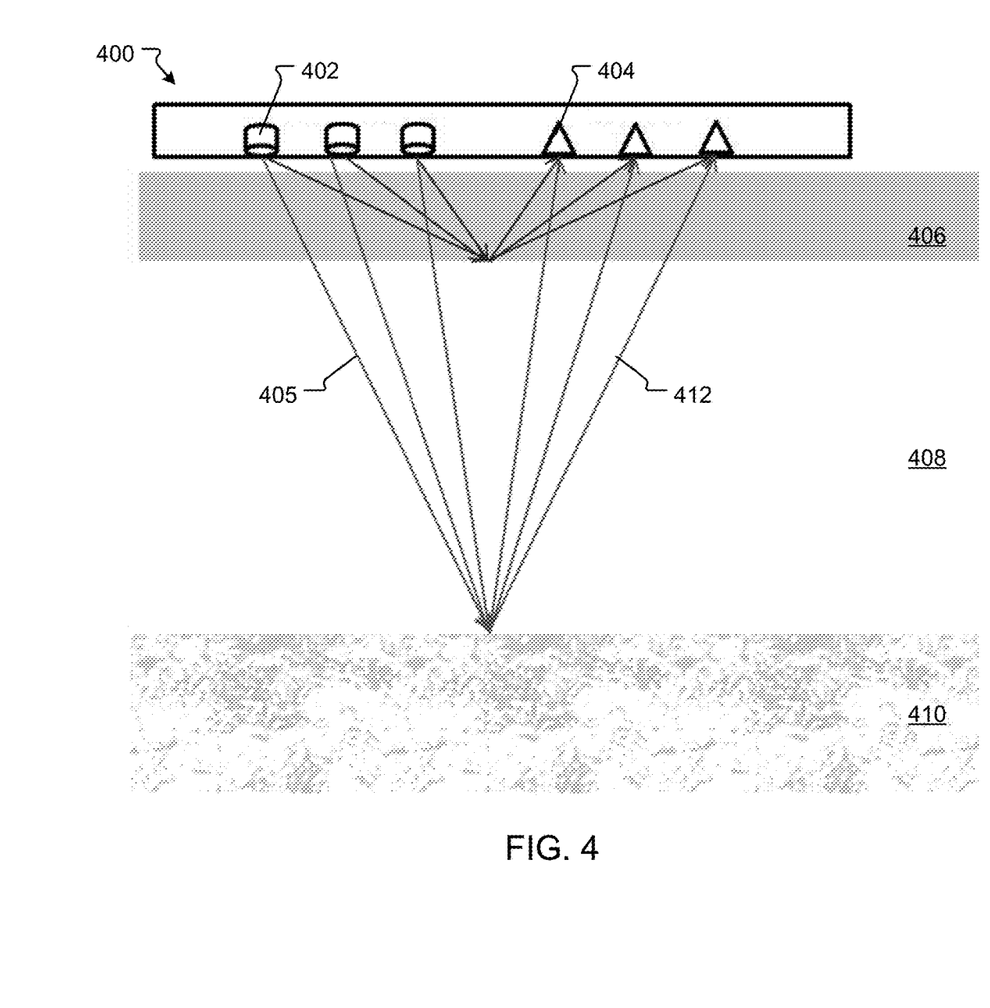

In some implementations, multiple transmitters are used in combination with an array of receivers. For example, in some implementations, each array may contain two, three, four, five, or more transmitters. Referring to FIG. 4, another example configuration of a cement evaluation tool 400 includes an array with multiple transmitters 402 positioned to the side of multiple receives 404. Acoustic energy 405 generated by the transmitters 402 reflects from the interfaces between the casing 406 and cement 408 or between the cement 408 and the formation 410. Returning energy 412 is detected and measured by the receivers 404.

In some implementations, one or more transmitters are placed between two arrays of receivers. For example, in some implementations, one transmitter may be positioned between two arrays of receivers. In some implementations, two or more transmitters are positioned between two arrays of receivers. In some implementations, transmitters and arrays of receivers are interleaved. For example, in some implementations, one or more transmitters are placed between a first and a second array of receivers, and one or more transmitters are placed between a second and a third array of receivers, and so forth.

The configuration shown in FIG. 4 may be used for common mid-point processing (CMP). The cement evaluation tool 400 may be moved along the length of a borehole during measurement. As the tool 400 is moving, the source energy emitted by the tool 400 covers, and thus overlap, the same section of the borehole numerous times and at different offsets. The measurements obtained by the receivers may be sorted to obtain common midpoint gathers. A group of traces may be constructed with a range of offsets that all sample the same location. The common midpoint gathers may be further analyzed to extract the amplitude versus offset (AVO) response of the casing/cement interface, as well as of the cement/formation interface. Because multiple measurements are obtained for a particular location, noise in the measurement data may be decreased, and the reliability of measurements increased.

Various properties of the cement and other structures can be obtained from the amplitude of the reflection from the casing/cement interface using an amplitude versus offset (AVO) equation. Such properties can include, for example, the compressional and shear wave slownesses and density of the structure. In particular, these properties may be determined according to the following equation:

$$PP = \frac{1}{2}(1 - 4\beta^2 p^2)\frac{\Delta\rho}{\rho} + \frac{1}{2\cos^2 i}\frac{\Delta\alpha}{\alpha} - 4\beta^2 p^2 \frac{\Delta\beta}{\beta},$$

where PP is the reflection coefficient for an incident primary wave (P-wave) and a reflected P-wave, $\beta$ is the shear wave velocity, $\alpha$ is the compressional wave velocity, $\rho$ is the density and $p$ is the ray parameter. Once $\alpha$, $\beta$, and $\rho$ are determined, the elastic moduli of the cement can be calculated. These include the bulk and shear moduli, and by extension the compressive strength of the cement.

For the cement/formation or cement/second casing interface, established seismic imaging algorithms may be used to image that interface, given the known properties of the casing and the measured cement properties. Deconvolution may be used to eliminate the effect of the casing and obtain images of the cement/formation. For instance, prior to analysis, deconvolution may be used to remove a reverberation of the casing from the measured returning energy in order to more accurately measure properties of the cement and formation. In some implementations, the cement evaluation tool directly measures the physical properties of the cement, rather than relying on the reverberation of the well casing or the attenuation of the acoustic wave. In some implementations, the tool may be used to produce inverted cement bond log estimates. This may be produced, for example, by performing an inversion of the AVO response of the casing/cement interface, as well as, of the cement/formation interface.

Figure 5:
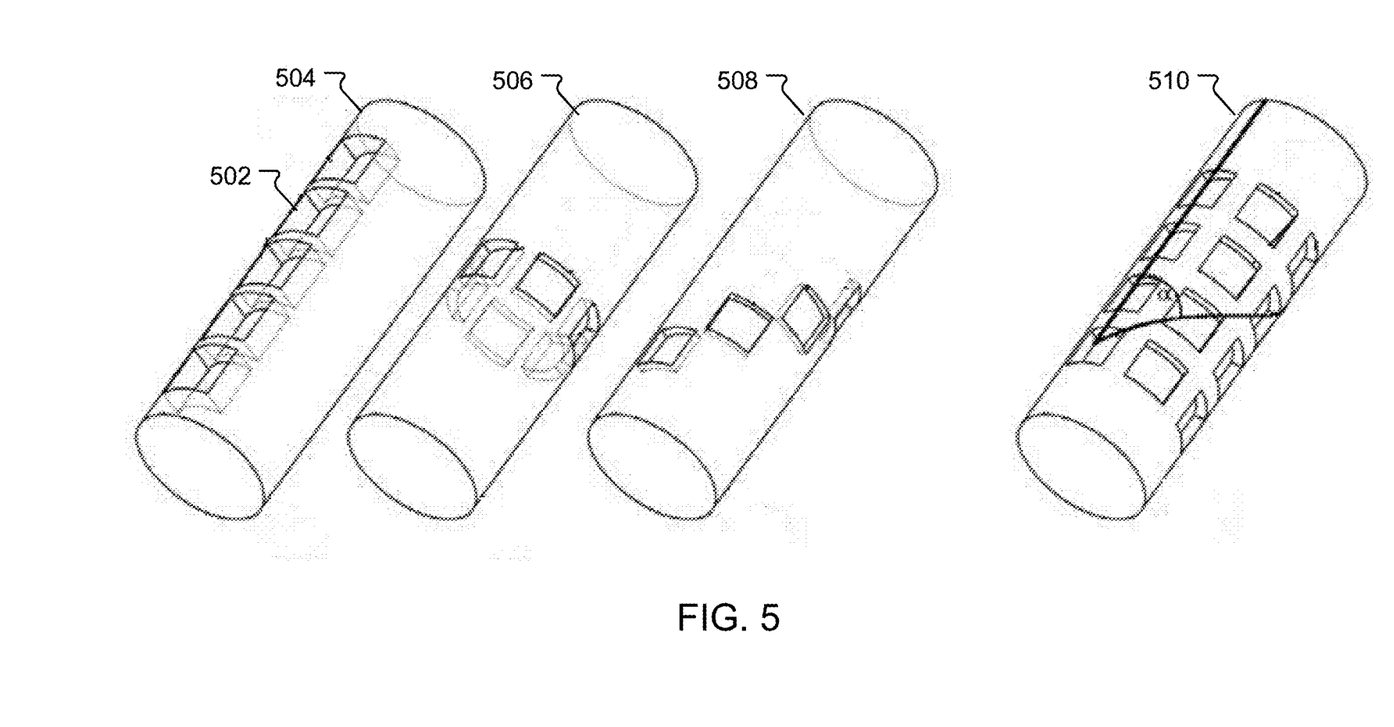
FIG. 5 shows example arrangements of arrays on a cement evaluation tool.

In some embodiments, an array is positioned on a cement evaluation tool in various ways, such that the array provides broad coverage around the tool. Referring to FIG. 5, example tools may have sensors (e.g., transmitters and receivers) and/or pads 502 arranged in a axial configuration 504, an azimuthal configuration 506, an axial and azimuthal combination configuration 508, or according to other layouts, such as a grid configuration 510.

Figure 6:
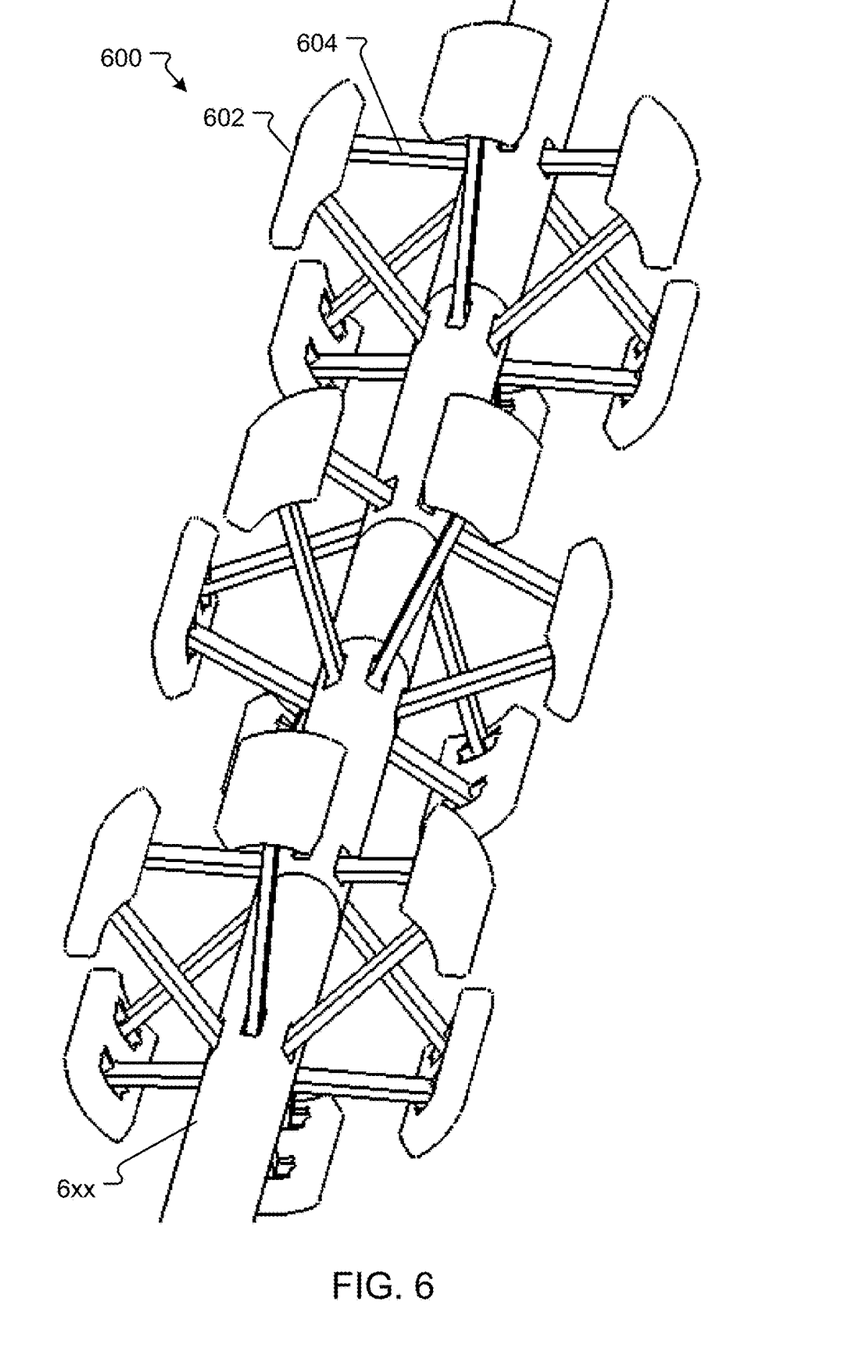
FIG. 6 shows an example arrangement of arrays on a cement evaluation tool.

A cement evaluation tool may include one or more arrays mounted to one or more retractable pad assemblies. Referring to FIG. 6, an example implementation to a cement evaluation tool 600 may include one or more arrays placed onto each of several pads 602. In some implementations, more than one transmitter or receiver may be disposed on each pad. Each pad 602 is mounted on an extendable arm 604, such that the pad 602 may be extended from the tool 600 to nearly contact or directly contact a well casing. In an example implementation, the tool 600 includes pads 602 mounted azimuthally in groups of six, each on extendable arms 604. Each array is azimuthally offset from the other arrays, such that the entire circumference of the borehole can be covered. Each group is axially offset from the other groups, such that an axial length of the borehole can also be covered. In FIG. 6, there are six pads 602 on each group, with a total of three groups, for a total of 18 pads.

In some implementations, an array that is mounted directly on the tool does not have direct contact with the well casing. The processing methodology described herein can still be used in these implementations, but the signal to noise ratio may be reduced in comparison, due to the additional reflection from the fluid/casing interface. However, these implementations may be preferred under certain circumstances, for instance when it is not practical or feasible for the array to directly contact the casing.

Figure 7:
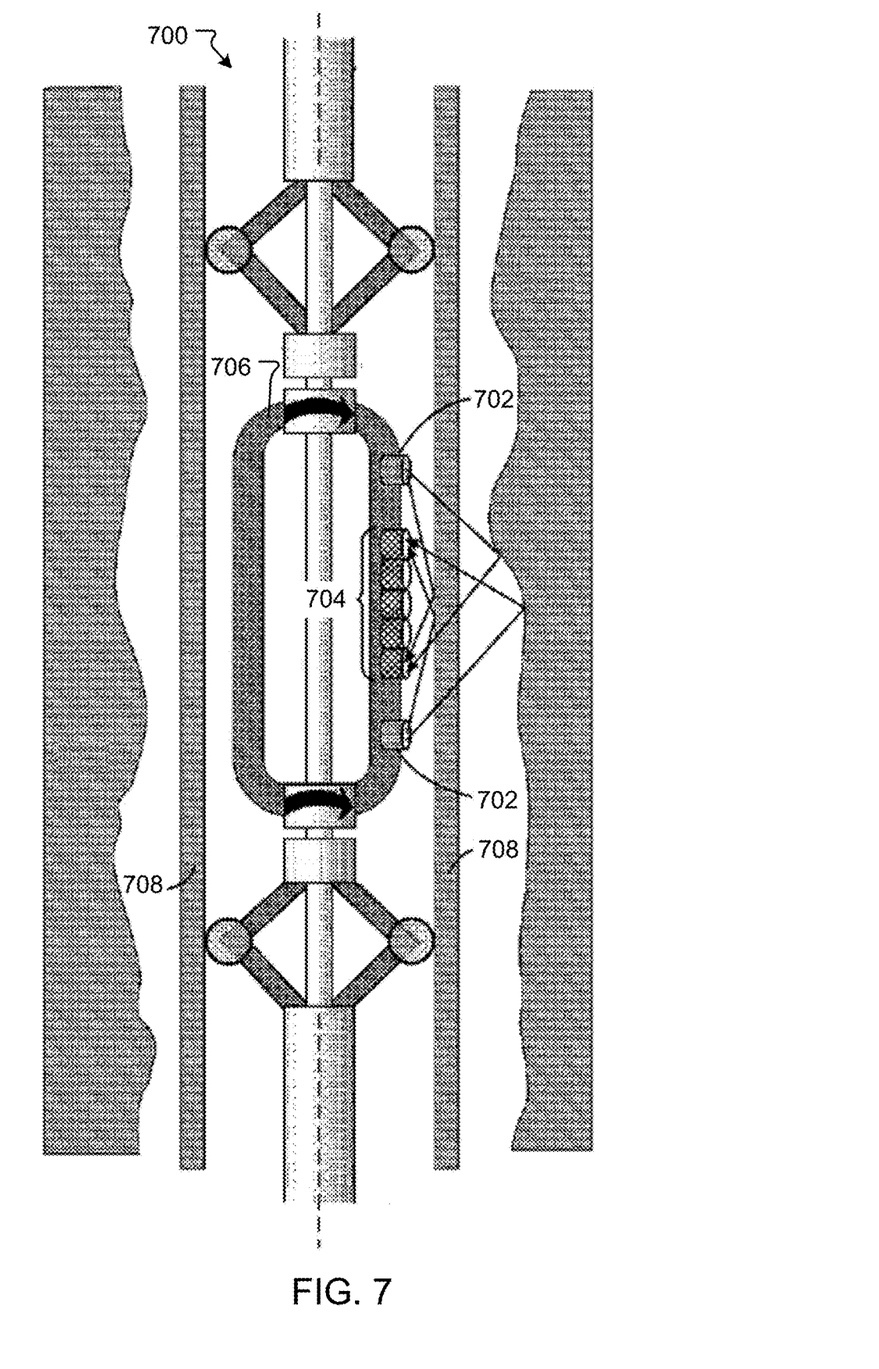
FIG. 7 shows an example implementation of a cement evaluation tool.

In some implementations, portions of the cement evaluation tool may rotate so that the transmitters and/or receivers may be re-positioned within the interior of the casing. For instance, referring to FIG. 7, an example implementation of a cement evaluation tool 700 is of a pitch-catch implementation that includes one or more transmitters 702 (two are shown) and two or more receivers 704 (five are shown) mounted to a rotating frame 706. The transmitters 702 and receivers 704 rotate with respect to a well casing 708, such that they are able to access any region along the inner circumference of the casing.

Figure 8:
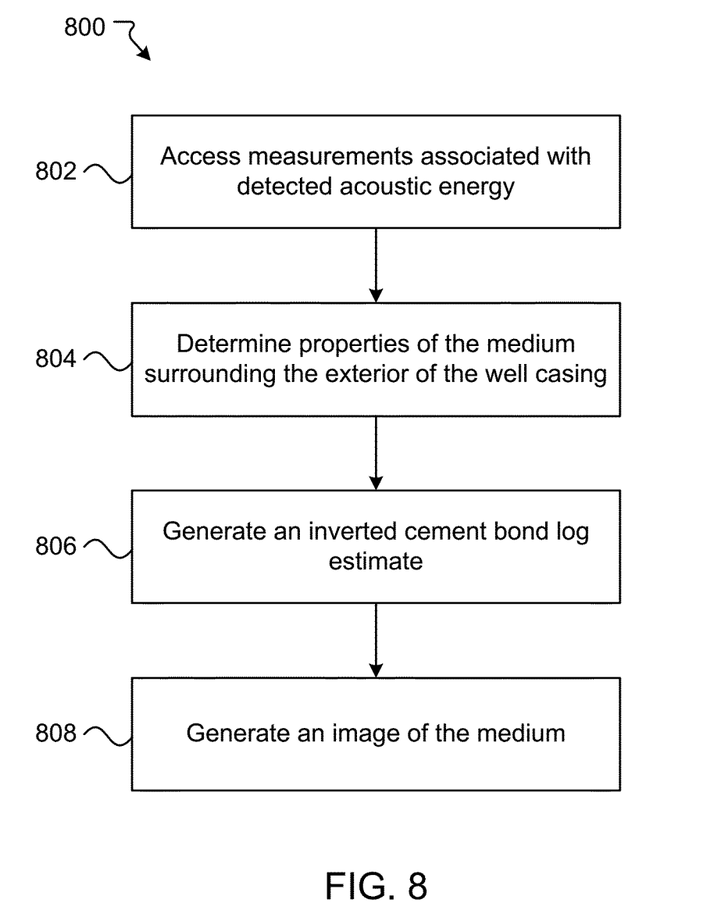
FIG. 8 is a flowchart showing an example technique for evaluating cement properties.

FIG. 8 is a flowchart showing an example process 800 for determining properties of a medium, e.g., cement, surrounding an exterior of a well casing. Some or all of the operations in the process 800 can be implemented by one or more computing devices. For example, the process 800 can be implemented by the computing subsystem 110 in FIG. 1A, the computing system 200 in FIG. 2, or by another type of system.

Some or all of the operations in the process 800 can be implemented by one or more computing devices that are embedded with, or otherwise operated in connection with, a logging tool. For example, the process 800 can be implemented in connection with the logging tool 102 in FIG. 1A, the cement evaluation tools in FIG. 3, 4, 5, 6, or, 7, or another type of tool. The cement evaluation tool may include one or more acoustic transmitters to transmit acoustic energy through a well casing to a medium, e.g., cement surrounding the exterior portion of the well casing. The cement evaluation tool may include two or more acoustic receivers to detect acoustic energy returning through the well casing. The transmitters and receivers can be operated within a wellbore that includes a well casing.

In some implementations, the process 800 includes additional, fewer, or different operations performed in the order shown in FIG. 8, or in a different order. Moreover, one or more of the individual operations or subsets of the operations in the process 800 can be performed in isolation, or as part of another process. Output data generated by the process 800, including output data generated by intermediate operations, can include stored, displayed, printed, transmitted, communicated or processed information.

In some implementations, some or all of the operations in the process 800 are executed in real time during a drilling operation or another type of operation performed in a well system. An operation can be performed in real time, for example, by performing the operation in response to receiving data (e.g., from a sensor or monitoring system) without substantial delay. An operation can be performed in real time, for example, by performing the operation while monitoring for additional data. Some real time operations can receive an input and produce an output during drilling operations; in some instances, the output is made available within a time frame that allows an operator (e.g., a human or machine operator) to respond to the output, for example, by modifying the drilling operation.

In some implementations, a cement evaluation tool is placed in a wellbore defined in a subterranean region that includes multiple subsurface layers. For example, the cement evaluation tool can be the logging tool 102 shown in FIG. 1A. The cement evaluation tool can be transported by a drilling assembly, by a wireline logging assembly, or other hardware. The cement evaluation tool can be operated at multiple tool depths in the wellbore, and each tool depth can represent a different logging point. The process 800 can be executed based on data for a single logging point or multiple logging points.

At 802, measurements associated with acoustic energy returned through a well casing and detected by two or more acoustic receivers based on operating one or more acoustic transmitters and the two or more receivers of a sensor array within a wellbore that includes the well casing are accessed. The measurements may include amplitudes of the detected acoustic energy.

At 804, properties of the medium, e.g., cement, surrounding the exterior portion of the well casing are determined based on the measurements and based on distances between the one or more acoustic transmitters and the two or more acoustic receivers. The properties of the medium can include compressional slowness, shear wave slowness, or density.

In some implementations, the properties of the medium can be determined based on a common midpoint analysis of the detected acoustic energy. In some implementations, the properties of the medium can be determined based on an amplitude versus offset analysis of the amplitudes and the distances. The amplitude versus offset analysis may include performing an inversion of the amplitude versus offset response. In some implementations, an inverted cement bond log estimate may be generated based on the inversion of the amplitude versus offset response, at 806. In some implementations, properties of the medium can be determined based on deconvolution that removes a reverberation of the well casing from the detected acoustic energy. In some implementations, an image of the medium can be generated based on the properties of the medium, at 808.

The techniques described above can be implemented in digital electronic circuitry, or in computer software, firmware, or hardware, including the structures disclosed in this specification and their structural equivalents, or in combinations of one or more of them. For example, an electronic processor may be used to control acoustic transmitters and receivers (e.g., by sending electronic command signals) in order to generate and detect acoustic energy. In another example, the electronic processor may be used to analyze and process data, for instance to determine information about the structures based on the detected returning acoustic energy and the arrangement of acoustic transmitters and acoustic receivers in the sensor array. In some implementations, the electronic processor may analyze the returning acoustic energy using specific techniques, for instance common midpoint analysis techniques, amplitude versus offset analysis techniques, one or more techniques described above, or other suitable techniques.

The term "electronic processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A client and server are generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). The relationship of client and server arises by virtue of computer programs running on the respective computers and having a client-server relationship to each other.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable subcombination.

A number of implementations have been described. Nevertheless, it will be understood that other implementations are also possible. For example, the method may include fewer steps than those illustrated or more steps that those illustrated. In addition the steps may be performed in the respective order or in different orders than illustrated.

In one general aspect, one or more properties of the medium surrounding the exterior portion of the well casing are determined based on measurements of the detected acoustic energy returning through the well casing and based on distances between the one or more acoustic transmitters and the two or more acoustic receivers.

In some aspects, a system includes a sensor array to be disposed within a wellbore that includes a well casing. The sensor array includes one or more acoustic transmitters to transmit acoustic energy through the well casing to a medium surrounding the exterior portion of the well casing, and two or more acoustic receivers to detect acoustic energy returning through the well casing. The system includes a computing system coupled with the sensor array. The computing system is operable to receive measurements of the detected acoustic energy based on operating the sensor array within the wellbore, and determine one or more properties of the medium surrounding the exterior portion of the well casing based on the measurements and based on distances between the one or more acoustic transmitters and the two or more acoustic receivers.

Implementations of these and other aspects may include one or more of the following features. The sensor array includes two or more acoustic transmitters. Each of the one or more acoustic transmitters and the two or more acoustic receivers is disposed at an end of a support member that radially extends from a tool body. The one or more acoustic transmitters and the two or more acoustic receivers are distributed axially along a tool body. The one or more acoustic transmitters and the two or more acoustic receivers are distributed azimuthally about a tool body.

Additionally or alternatively, implementations of these and other aspects may include one or more of the following features. The system includes another sensor array. The other sensor array includes one or more other acoustic transmitters and two or more other acoustic receivers. The one or more other acoustic transmitters and the two or more other acoustic receivers are distributed azimuthally about the tool body, and the other sensor array is axially offset from the sensor array. The other sensor array is azimuthally offset from the sensor array.

Additionally or alternatively, implementations of these and other aspects may include one or more of the following features. The measurements include amplitudes of the detected acoustic energy, and the computing system determines the one or more properties of the medium surrounding the exterior portion of the well casing based on an amplitude versus offset analysis of the amplitudes and the distances. The amplitude versus offset analysis comprises performing an inversion of an amplitude versus offset response. The medium comprises cement, and the computing system generates an inverted cement bond log estimate based on the inversion of the amplitude versus offset response.

Additionally or alternatively, implementations of these and other aspects may include one or more of the following features. The computing system determines the one or more properties of the medium based on a common midpoint analysis of the detected acoustic energy. The computing system determines the one or more properties of the medium based on deconvolution that removes a reverberation of the well casing from the detected acoustic energy. The computing system generates an image of the medium surrounding the exterior portion of the well casing based on the one or more properties of the medium. The one or more properties comprises one or more of compressional slowness, shear wave slowness, or density of the medium.

In some aspects, measurements associated with acoustic energy returned through a well casing and detected by two or more acoustic receivers based on operating one or more acoustic transmitters and the two or more acoustic receivers of a sensor array within wellbore that includes the well casing is accessed, and one or more properties of the medium surrounding the exterior portion of the well casing is determined based on the measurements and based on distances between the one or more acoustic transmitters and the two or more acoustic receivers.

Implementations of these and other aspects may include one or more of the following features. The measurements include amplitudes of the detected acoustic energy. The one or more properties of the medium surrounding the exterior portion of the well casing are determined based on an amplitude versus offset analysis of the amplitudes and the distances. The amplitude versus offset analysis includes performing an inversion of an amplitude versus offset response. The medium includes cement, and an inverted cement bond log estimate is generated based on the inversion of the amplitude versus offset response.

Additionally or alternatively, implementations of these and other aspects may include one or more of the following features. Determining the one or more properties of the medium includes determining the one or more properties based on a common midpoint analysis of the detected acoustic energy. Determining the one or more properties of the medium includes determining the one or more properties based on deconvolution that removes a reverberation of the well casing from the detected acoustic energy. An image of the medium surrounding the exterior portion of the well casing is generated based on the one or more properties of the medium. The one or more properties includes one or more of compressional slowness, shear wave slowness, or density of the medium.

Other embodiments are within the scope of the following claims.

What is claimed is:

1. A system comprising:
   a sensor array to be disposed within a wellbore comprising a well casing, the sensor array comprising:
     one or more acoustic transmitters to transmit acoustic energy through the well casing to a medium surrounding the exterior portion of the well casing, and
     two or more acoustic receivers to detect acoustic energy returning through the well casing, wherein each of the one or more acoustic transmitters and the two or more acoustic receivers is disposed at an end of a support member that radially extends from a tool body; and
   a computing system coupled with the sensor array, the computing system is configured to:
     receive measurements of the detected acoustic energy based on operating the sensor array within the interior portion of the well casing, and
     determine one or more properties of the medium surrounding the exterior portion of the well casing based on the measurements and based on distances between the one or more acoustic transmitters and the two or more acoustic receivers, wherein the one or more properties comprises an impedance of the medium.

2. The system of claim 1, wherein the sensor array comprises two or more acoustic transmitters.

3. The system of claim 1, wherein the one or more acoustic transmitters and the two or more acoustic receivers are distributed axially along a tool body.

4. The system of claim 1, wherein the one or more acoustic transmitters and the two or more acoustic receivers are distributed azimuthally about a tool body.

5. The system of claim 4, further comprising:
another sensor array comprising one or more other acoustic transmitters and two or more other acoustic receivers, wherein the one or more other acoustic transmitters and the two or more other acoustic receivers are distributed azimuthally about the tool body, and the other sensor array is axially offset from the sensor array.

6. The system of claim 1, wherein the measurements include amplitudes of the detected acoustic energy, and the computing system is configured to determine the one or more properties of the medium surrounding the exterior portion of the well casing based on an amplitude versus offset analysis of the amplitudes and the distances.

7. The system of claim 1, wherein the computing system is configured to determine the one or more properties of the medium based on a common midpoint analysis of the detected acoustic energy.

8. The system of claim 1, wherein the computing system is configured to determine the one or more properties of the medium based on deconvolution that removes a reverberation of the well casing from the detected acoustic energy.

9. The system of claim 1, wherein the one or more properties comprises one or more of compressional slowness, shear wave slowness, or density of the medium.

10. A method comprising:
accessing measurements associated with acoustic energy returned through a well casing and detected by two or more acoustic receivers based on operating one or more acoustic transmitters and the two or more acoustic receivers of a sensor array within a wellbore comprising the well casing, wherein each of the one or more acoustic transmitters and the two or more acoustic receivers is disposed at an end of a support member that radially extends from a tool body; and
determining, by operation of data processing apparatus, one or more properties of the medium surrounding the exterior portion of the well casing based on the measurements and based on distances between the one or more acoustic transmitters and the two or more acoustic receivers, wherein the one or more properties comprises an impedance of the medium.

11. The method of claim 10, wherein the measurements include amplitudes of the detected acoustic energy, and the method further comprises determining the one or more properties of the medium surrounding the exterior portion of the well casing based on an amplitude versus offset analysis of the amplitudes and the distances.

12. The method of claim 10, wherein determining the one or more properties of the medium comprises determining the one or more properties based on a common midpoint analysis of the detected acoustic energy.

13. The method of claim 10, wherein determining the one or more properties of the medium comprises determining the one or more properties based on deconvolution that removes a reverberation of the well casing from the detected acoustic energy.

14. The method of claim 10, wherein the one or more properties comprises one or more of compressional slowness, shear wave slowness, or density of the medium.

15. A non-transitory computer-readable medium encoded with instructions that, when executed by data processing apparatus, cause the data processing apparatus to perform operations comprising:
accessing measurements associated with acoustic energy returned through a well casing and detected by two or more acoustic receivers based on operating one or more acoustic transmitters and the two or more acoustic receivers of a sensor array within a wellbore that includes the well casing, wherein each of the one or more acoustic transmitters and the two or more acoustic receivers is disposed at an end of a support member that radially extends from a tool body; and
determining, by operation of data processing apparatus, one or more properties of the medium surrounding the exterior portion of the well casing based on the measurements and based on distances between the one or more acoustic transmitters and the two or more acoustic receivers, wherein the one or more properties comprises an impedance of the medium.

16. The non-transitory computer-readable medium of claim 15, wherein the measurements include amplitudes of the detected acoustic energy, and the method further comprises determining the one or more properties of the medium surrounding the exterior portion of the well casing based on an amplitude versus offset analysis of the amplitudes and the distances.

17. The non-transitory computer-readable medium of claim 15, wherein determining the one or more properties of the medium comprises determining the one or more properties based on a common midpoint analysis of the detected acoustic energy.

18. The non-transitory computer-readable medium of claim 15, wherein determining the one or more properties of the medium comprises determining the one or more properties based on deconvolution that removes a reverberation of the well casing from the detected acoustic energy.

19. The non-transitory computer-readable medium of claim 15, wherein the one or more properties comprises one or more of compressional slowness, shear wave slowness, or density of the medium.

* * * * *